United States Patent [19]

Zepp et al.

[11] 4,115,009
[45] Sep. 19, 1978

[54] OPTICAL SIGHT TUBE FOR FLOWING FLUID MATERIALS

[75] Inventors: Lawrence C. Zepp, Claremont; Marston D. Mosteller, Alhambra, both of Calif.

[73] Assignee: Bindicator Company, Port Huron, Mich.

[21] Appl. No.: 777,075

[22] Filed: Mar. 14, 1977

[51] Int. Cl.² ............................................. G01N 21/26
[52] U.S. Cl. ................................. 356/201; 356/181
[58] Field of Search ............. 356/181, 201, 207, 208, 356/244, 246; 250/343, 373, 573, 576

[56] References Cited

U.S. PATENT DOCUMENTS

| | | | |
|---|---|---|---|
| 2,649,011 | 8/1953 | Black | 356/246 |
| 3,628,028 | 12/1971 | Thorsheim | 250/576 |
| 3,773,424 | 11/1973 | Selgin | 356/181 |

Primary Examiner—F. L. Evans
Attorney, Agent, or Firm—Barnes, Kisselle, Raisch & Choate

[57] ABSTRACT

Apparatus for measuring a preselected characteristic, such as moisture, of viscous and/or absorption fluids in which an open hollow tube of optically reflective material is disposed within a fluid conduit closely adjacent an optical window to define a test material flow path between the window and reflector. A measurement beam incident upon the reflector tube from externally of the conduit through the window and test material is reflected thereby back through the material and window to detection apparatus. In alternative embodiments, the reflector tube is fixedly mounted coaxially with the conduit to define a fixed window/reflector separation, or is rotatably mounted eccentrically of the conduit axis for adjustment of the window/reflector separation.

11 Claims, 10 Drawing Figures

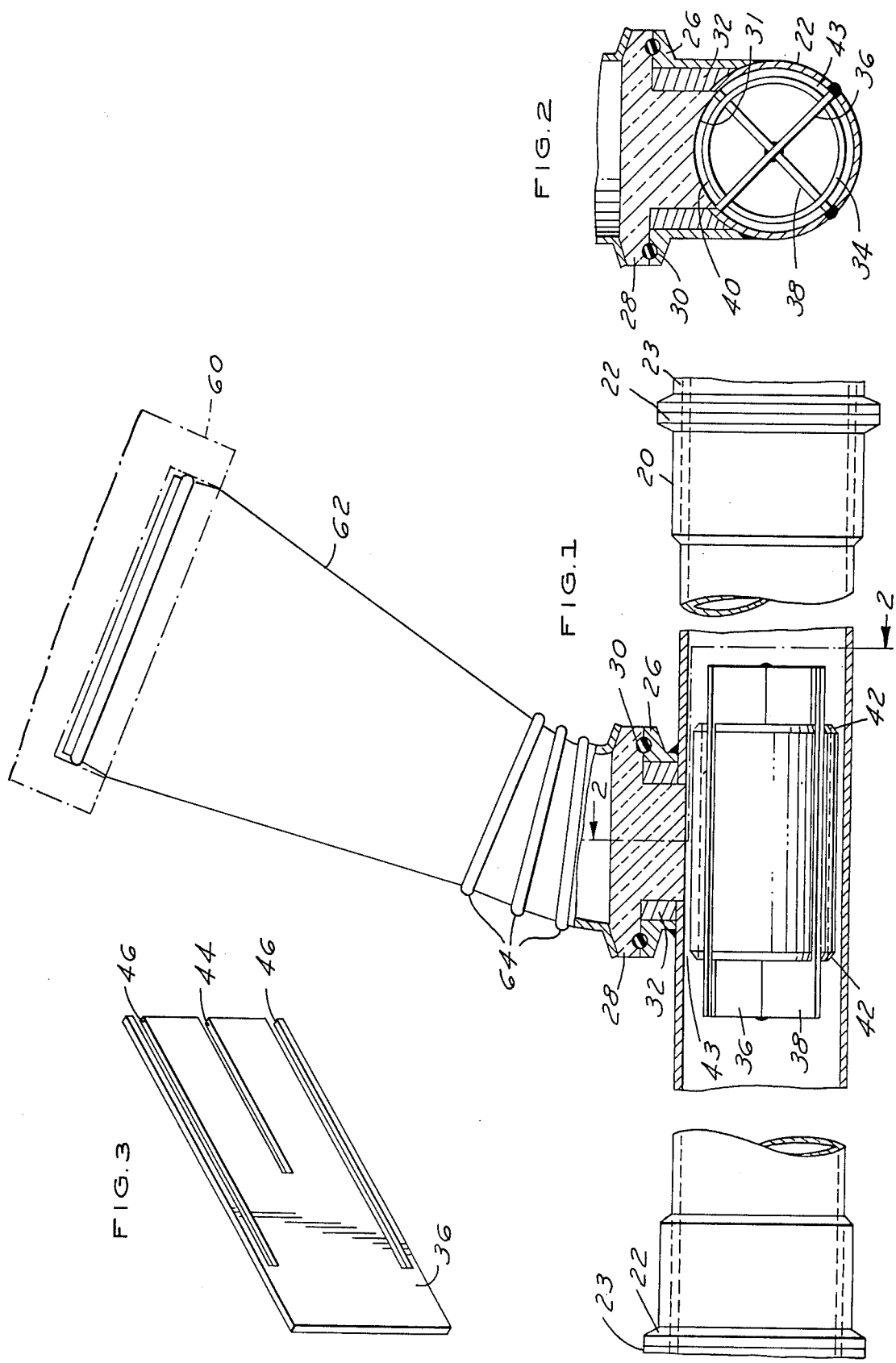

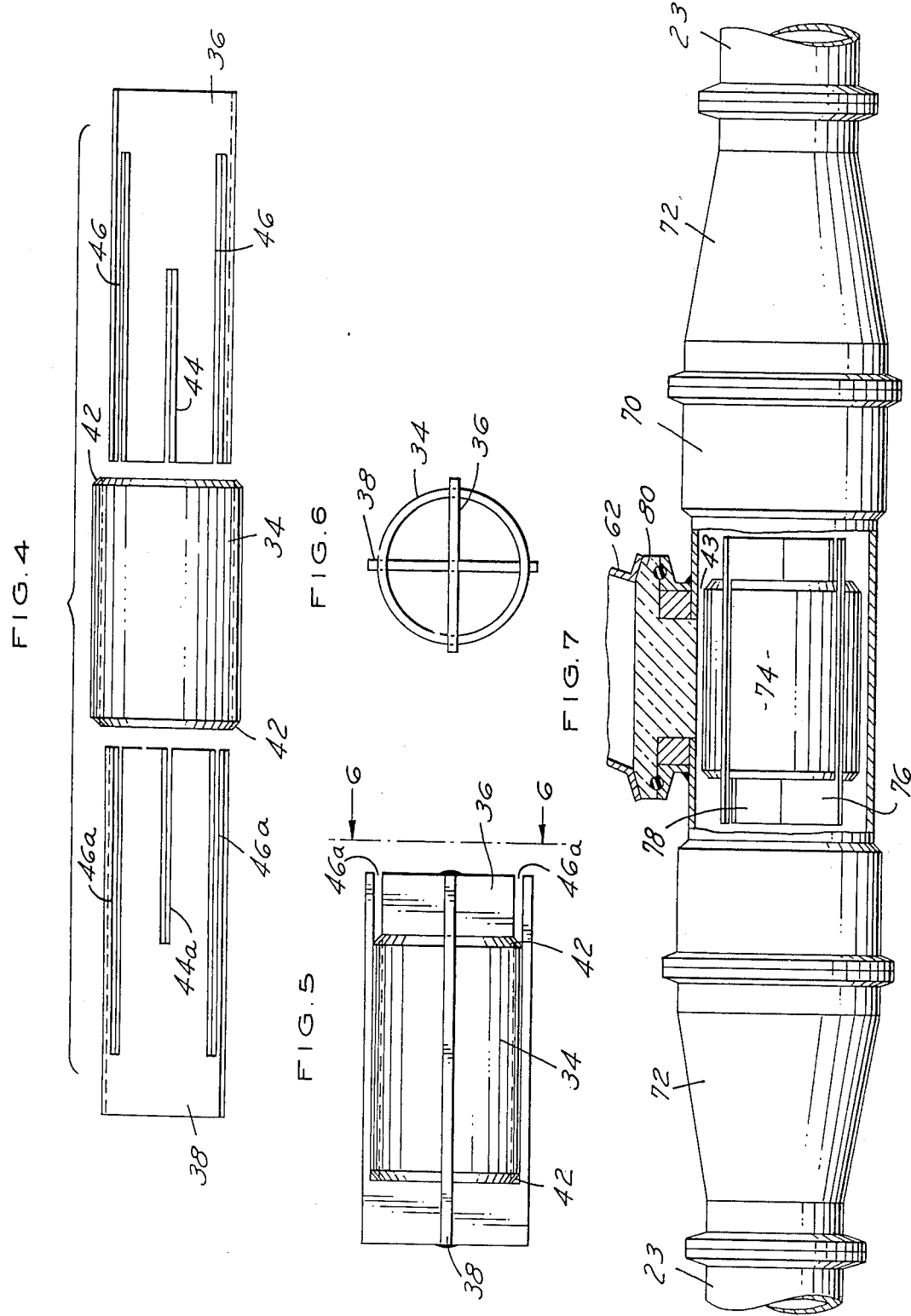

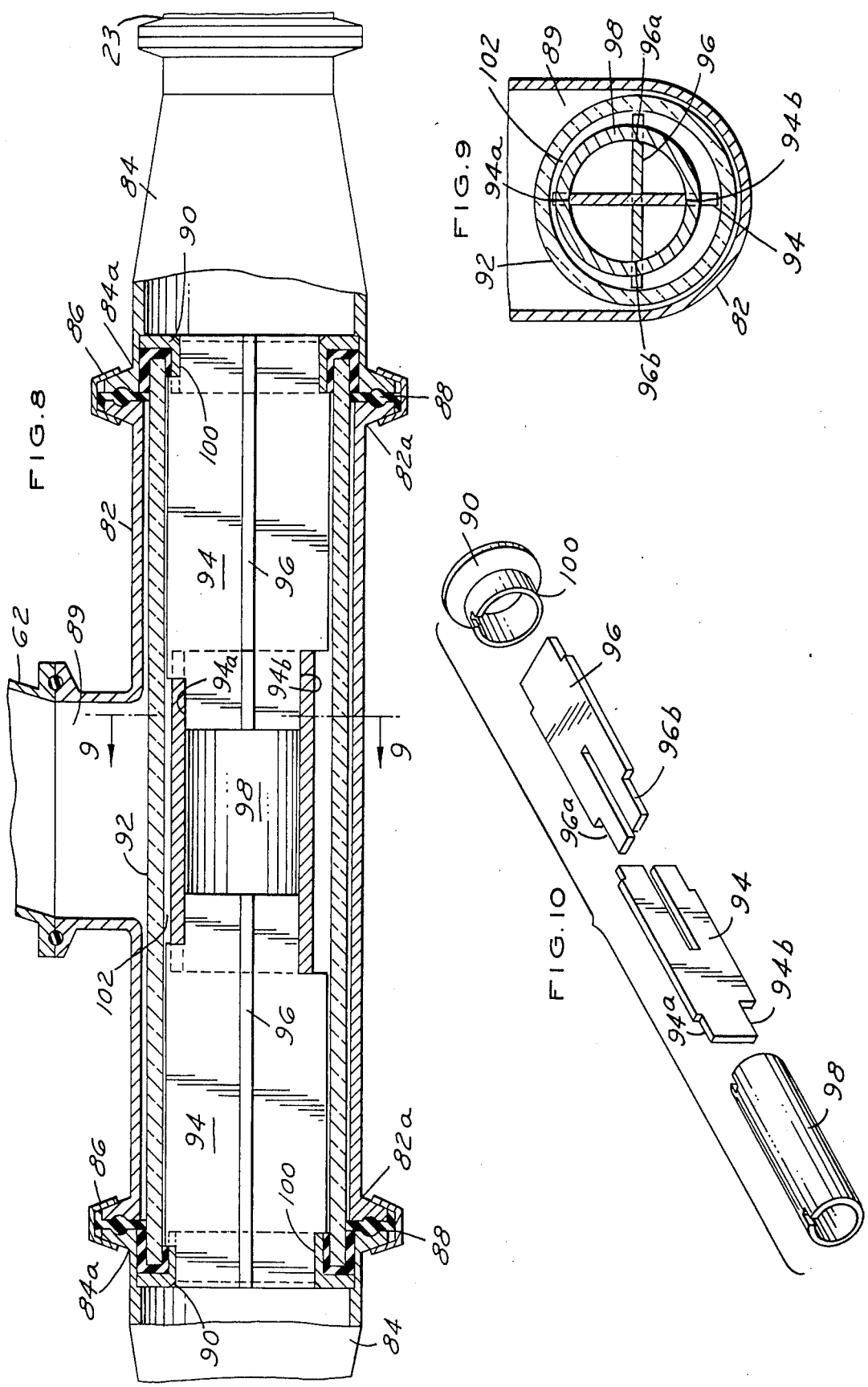

OPTICAL SIGHT TUBE FOR FLOWING FLUID MATERIALS

The present invention relates to optical test equipment and, more particularly, to instruments for measuring a preselected characteristic of viscous and/or highly absorptive fluid materials, such as the moisture content thereof, using optical absorption/reflection techniques.

Viscous fluid materials, such as fats, oils, syrups, licorice and peanut butter, are often highly absorptive to electromagnetic energy in the optical or, more specifically, the infrared frequency range. Thus, when it is attempted to measure characteristics of such materials, such as moisture content, on a continuous basis from externally of the material flow path using well-known optical absorption/reflection techniques, most of the measurement beam energy is absorbed and insufficient energy is reflected by the material to obtain a reliable reading. Attempts to locate part or all of the instrumentation within the fluid path have lead to blockage and clogging due to material viscosity.

Accordingly, objects of the present invention are to provide an apparatus for optically measuring characteristics of flowing viscous and/or highly absorptive material which is readily and uniquely adapted for use with otherwise conventional absorption/reflection measuring techniques, which is economical to manufacture and install, and which presents only minimal impedance to fluid flow.

It is another object of the invention to provide an apparatus of the described type which may be readily and rapidly adjusted at the measurement site for materials of different viscosities and/or absorptivities.

The invention, together with additional objects, features and advantages thereof, will be best understood from the following description when read in conjunction with the accompanying drawings in which:

FIG. 1 is an elevational, partially sectional view of one embodiment of the invention;

FIG. 2 is a sectional view taken along the line 2—2 of FIG. 1;

FIG. 3 is a perspective view of one element in the embodiment of FIG. 1;

FIG. 4 is an exploded view of a portion or subassembly in the embodiment of FIG. 1;

FIGS. 5 and 6 are respective elevational and side views of the subassembly of FIG. 4;

FIG. 7 is an elevational view of a second embodiment of the invention which is specifically adapted for use with high-viscosity fluids;

FIG. 8 is an elevational view of a further embodiment of the invention which is adjustable for fluids of differing viscosities and/or absorptivities;

FIG. 9 is a sectional view taken along the line 9—9 of FIG. 8; and

FIG. 10 is an exploded perspective view of a portion of the embodiment of FIG. 8.

Referring to FIGS. 1 and 2, one embodiment of the fluid sight tube in accordance with the invention comprises an elongate hollow cylindrical conduit section 20 having flanges 22 at each end for coaxial connection of conduit section 20 in a confined fluid flow line or path 23 using suitable clamps or the like (not shown) such that fluid may flow under pressure and temperature conditions through the conduit section in the direction of its axis. A window mounting bracket 26 encompasses an aperture in a radial wall in conduit section 20. A generally T-shaped transparent window 28 is adhered or otherwise fixedly mounted onto bracket 26 with a resilient sealing ring 30 disposed therebetween and, as best seen in FIG. 2, extends into the conduit section aperture to terminate in an arcuate face 31 cocylindrically with the inside diameter of conduit section 20. A sleeve or bushing 32 may be disposed between the radial portion of window 28 and bracket 26. Conduit section 20 and bracket 26 may be fabricated of suitable opaque material consistent with the sanitary requirements, etc. of the remainder of the fluid line, preferably of stainless steel. Window 28 may be machined from a rod of suitable transparent "Pyrex" glass material.

A hollow tube 34 is carried by opposed orthogonally internested plates 36,38 within conduit section 20 coaxially therewith and has an outer reflective surface 40 disposed closely adjacent but spaced from arcuate inner window face 31. The outer edges of plates 36,38 engage the inside wall of conduit section 20 and are affixed thereto as by welding. Tube 34 and plates 36,38 are relatively thin in the dimension transverse to material flow and tube 34 is open at both ends so that the tube and mounting structure present only minimal impedance to material flowing through conduit section 20. Tube 34 is outwardly beveled at both ends 42 (FIG. 1) both further to reduce the impedance to fluid flow and to help divert fluid material into the test path or region 43 between window and reflector surfaces 31,40. The dimension of test material path 43 transverse to the direction of material flow is small as compared with the transverse dimension or diameter of conduit section 20. Thus, only a relatively small amount of material is diverted through the test path past window 28, while the bulk of material flows through tube 34 remotely of the window. Reflector tube 34 may be of any suitable material having a reflective outer surface which may be polished or deposited thereon. Preferably the reflector tube is fabricated entirely of reflective material, such as from "Teflon" tube stock having a relatively smooth outer surface.

The details of plates 38,40 and the assembly thereof with tube 34 will best be appreciated with reference to FIGS. 3–6. Plate 36 (FIG. 3) is rectangular and has a blind central slot 44 opening at one of the narrow plate side edges and extending for about half of the plate length. Additional parallel slots 46 extend adjacent each outer edge of plate 36 for a substantial portion of its length and are separated from each other by a distance equal to the inside diameter of tube 34. Plate 38 is identical to plate 36, having a central slot 44a and outer parallel slots 46a. Slots 44,44a are dimensional to the thickness of plates 36,38, and slots 46,46a are dimensional to the thickness of tube 34. In assembly, slots 44,44a are aligned with each other and slots 46,46a are aligned with the axial edges of tube 34 such that, as plates 36,38 are axially internested, slots 46,46a capture the wall of tube 34. Plates 36,38 are positioned orthogonally and may be permanently joined, as by welding at one or both axial ends. The assembly comprising tube 34 and plates 36,38 is then ready for mounting into conduit section 20 (FIG. 1).

An optical instrument case or head 60 is suitably mounted (by means not shown) and optically coupled to window 28 by a conical opaque and dust-tight light shield 62. Shield 62, which may be of sheet aluminum or rubber impregnated fabric for example, is sealed at its repsective ends to window 28 and head 60, and is internally coated with optically absorptive material. Corrugations 64 or the like are provided in shield 62 so that the shield may be bent in an arc around window 28 to accommodate a convenient location for head 60 such that a measurement beam from head 60 is incident upon the material in test space 43 from a direction generally orthogonal to the direction of material flow.

Head 60 may include suitable elements, such as a light source and a photocell, for affecting the desired material characteristic measurement, and hence the components housed therein do not per se constitute part of the present invention. The head 60 shown for illustration in the drawings is that used in moisture measurement apparatus heretofore marketed by applicant's assignee under the trademark "MR System". Briefly described, the "MR System" unit is designed to measure the moisture content of materials using a reflection/absorption measuring technique. A stabilized source of near-infrared light emits energy which is focused by a lens onto the material at the surface of window 28. Light reflected by the material is collected by the lens and directed onto a lead-sulphide photocell. A pair of narrow band interference filters are alternately passed through the reflected beam so that the cell is alternately supplied with energy of a selected first wavelength sensitive to material moisture content and a selected second wavelength sensitive to material reflectivity but independent of moisture content. Head 60 may be connected to appropriate electronic circuitry to separate and compare the two signals, and thereby yield an accurate indication of material moisture.

It had heretofore been found that measurement accuracy is enhanced when the sight window is disposed at angle with respect to the beam path so that radiant energy directly reflected by the window surfaces, and independent of material moisture, will be directed away from the measurement unit. Thus head 60 is carried at a preferred angle of about $22\frac{1}{2}°$ with respect to the axis of window 28. Furthermore, as noted hereinabove, the inside surface of shield 62 is preferably coated with light-absorptive material. Hence, only diffuse or scattered reflections from the material surface would be received by the measurement head. The window angle of $22\frac{1}{2}°$ was empirically selected to yield diffuse material reflection of sufficient intensity for measurement purposes, and yet insure that direct reflections are absorbed by the tube wall. It had also been found that best results are obtained when the radiant energy is focused to the material/window interface. Thus, the length of light shield 62 preferably is chosen to correspond with the particular head 60 with which it is to be used to place the beam focus at the desired location. This length is 230 (plus or minus 25) millimeters in the case of the "MR System" head 60.

In accordance with the present invention, it has been recognized that head 60 described above, and others of similar type, may be readily used with highly absorptive materials, i.e., materials having low optical reflectivity, by providing reflective surface 40 closely adjacent window 28 so that a measurement beam from head 60 through window 28 traverses test material between window and reflective surfaces 31,40 and is reflected by surface 40 back through the test material and window to the head detection components. Material characteristics, specifically moisture content, may then be measured by head 60 as a function of material absorptivity rather than material reflectivity. The distance between window surface 31 and reflective surface 40 is empirically selected on the basis of material absorptivitiy and viscosity. For highly absorptive materials it is desirable to locate reflective surface 40 as closely as possible to the window to reduce the depth of material which must be traversed by the measurement beam, while for high viscosity materials it may be desirable to increase the intersurface distance to prevent clogging. Thus, the surface separation is often a trade-off between these two considerations. For margarine, satisfactory results have been obtained using an intersurface spacing of 0.060 inch, as compared with a conduit inside diameter of about two inches, and filters in head 60 having nominal center wavelengths of 1.94 and 1.80 microns for readings dependent upon and independent of moisture content, respectively.

The embodiment of the invention hereinabove described in connection with FIGS. 1-6 is particularly well adapted for measuring characteristics of optically absorptive fluid materials having low and medium viscosities because the effective cross section transverse to material flow of tube 34 and plates 36,38, which is small as compared with the cross sectional area of conduit 20, has negligible blockage effect. An alternative embodiment of the invention which is particularly well suited for use with fluids of higher viscosities is shown in FIG. 7 and comprises a cylindrical conduit section 70 of increased inside diameter as compared with conduit section 20 of FIG. 1, and tapering end sections 72 for adapting section 70 to material flow lines 23 of the lesser diameter. Conduit sections 70, 72 are joined by removable clamps (not shown) or by other means such as welding. The remainder of the embodiment of FIG. 7, i.e., reflective tube 74, orthogonal internested plates 76,78 and window 80 are substantially identical to corresponding elements of the embodiment of FIGS. 1-6 but have corresponding enlarged dimensions to accommodate the enlarged diameter of conduit section 70. Preferably, the net effective cross sectional area of conduit section 70 in a direction transverse to material flow therethrough, i.e., the inside cross sectional area of the conduit section less the effective cross sectional area of tube 74 and plates 76,78, is equal to or greater than the corresponding cross sectional area of main flow line 23. Thus, tube 74 and plates 76,78 have no blockage effect upon material flow. The separation between window 80 and tube 74 is selected on the basis of material absorptivity and reflectivity as hereinabove discussed.

The specific embodiments of the invention illustrated in FIGS. 1-7 is the subject of the copending application of Walter E. Levine Ser. No. 777,433 filed Mar. 14, 1977 and assigned to the assignee hereof.

The embodiments of the invention thus far described envision a fixed window/reflector spacing which is built into the sight tube assembly at the time of manufacture. Should it later become desirable to use the flow line into which the invention has been installed for a different fluid requiring a different window/reflector spacing, the sight tube would have to be refurbished or, preferably, replaced by a sight tube specifically designed for the particular material. Yet another embodiment of the invention illustrated in FIGS. 8-10 includes means for selectively adjusting the window/reflector spacing at the installation site for fluids of differing absorptivities and/or viscosities. A cylindrical conduit section 82 has reduction sections 84 mounted at either end by V-clamps 86 with suitable ring seals 88 disposed therebetween. As with the embodiments hereinbefore described, conduit sections 82,84 are to be connected in a confined fluid path or line 23. As aperture 89 in the wall of conduit section 82 communicates with optical head 60 (FIG. 1) through shield 62 as hereinabove described. A pair of collars 90 are press fitted into reduction conduit sections 84 and rest against corresponding shoulders therein. An open hollow cylindrical window 92 of translucent material is held between collars 92 coaxially with conduit section 82. Compression seals are disposed between collars 90 and the opposing edges of said window 92 to effectively seal the enclosed fluid path from conduit aperture 89. Index marks and suitable graduations are stamped into adjacent lips 82a,84a of conduit sections 82,84 for purposes to be described hereinafter.

An open hollow tube 98 of optically reflective material is carried within conduit section 82 and window 92 by pairs of thin orthogonally positioned, axially internested plates 94,96. Recessed shoulders on each radially outer edge of plates 94,96 engage corresponding edges of reflective tube 98 and an axially extending flange 100 on collar 90, shoulders on at least one plate (94) being received into corresponding notches in tube 98 and collar flange 100 to prevent rotation of the tube with respect to the collar. As will be best appreciated from FIGS. 8 and 9, the tube-support shoulders 94a,94b of plate 94 are separated from each other by a distance equal to the inside diameter of tube 98 but penetrate the width of plate 94 unequal distances, i.e., the support surfaces of shoulders 94a,94b are centered on an axis which is parallel to but spaced from the longitudinal axis of plate 94. Tube-support shoulders 96a,96b in plate 96 are symmetrical about the plate longitudinal axis. Thus, the axis of tube 98 is offset in assembly from the axis of window 92 and conduit section 82 by symmetric plate shoulders 94a,94b. This axial offset is particularly advantageous because it permits the effective window/reflector separation, i.e., the spacing 102 between window 92 and tube 98 as viewed through aperture 89, to be adjusted or readjusted at an installation site. More specifically, with clamps 86 loosened or removed, the reflector mounting structure comprising plates 94, 96, collars 90 and conduit sections 84 is effectively disengaged from conduit section 82, and the reflector and mounting structure (with window 92) may be rotated within conduit section 82 about the axis thereof. As best seen in FIG. 9, separation 102 between reflector tube 98 and window 92 beneath aperture 89 varies with such rotation, whereby such separation 102 may be accurately determined and set by comparing graduations on lip 84a with an index mark on lip 82. Clamps 86 may then be replaced or tightened and the apparatus will be ready for operation at the desired window/reflector spacing. Of course, the reflective surface of tube 98 will be substantially but not exactly parallel to the inside surface of window 92 for most window/reflector spacings. However, because measurement head 60 (FIG. 1) operates upon diffusely reflected rather than directly reflected energy from the reflective surface, this presents no difficulty. In addition to the adjustability feature outlined above, the embodiment of FIGS. 8-10 has the additional advantage of replacing the specially fabricated windows 28 (FIG. 1) and 80 (FIG. 7) with stamped collars 90 and a less expensive window 92 which may be cut from a length of standard tube stock.

The invention claimed is:

1. Apparatus for optically measuring a preselected characteristic of fluids flowing in a confined path comprising a cylindrical conduit disposed to define at least a portion of said confined fluid path, means providing an optical window in a wall of said conduit, means for optically detecting said material characteristic through said window, reflective means providing an arcuate reflective surface adjacent said window and defining a test material flow path between said surface and said window, said reflective means being mounted within said conduit by means engaging an inside cylindrical wall of said conduit, and means for selectively adjusting the spacing between said window and said reflective surface including means for selectively disengaging said mounting means from said conduit wall, said mounting means being rotatable coaxially within said conduit when disengaged from said conduit wall thereby to vary said spacing, said reflective means being adapted to reflect measurement optical beams incident upon said surface through said window and test material back through test material and said window.

2. The apparatus set forth in claim 1 wherein the material-contacting surface of said window opposite said reflect surface is arcuate coaxially with said cylindrical conduit.

3. The apparatus set forth in claim 2 wherein said conduit is cylindrical, said window being disposed in a radial wall of said cylindrical conduit, and wherein said reflective surface is arcuate about an axis displaced from the axis of said conduit.

4. Apparatus for optically measuring a preselected characteristic of fluids flowing in a confined path comprising a cylindrical conduit disposed to define at least a portion of said confined fluid path, means providing an optical window in a radial wall of said conduit, means for optically detecting said material characteristic through said window, reflective means comprising a hollow cylindrical tube and means for mounting said tube such that an outer reflective surface is disposed adjacent said window to define a test material flow path between said surface and said window and the central axis of said tube is offset from the central axis of such conduit, and means for selectively adjusting the spacing between said window and said reflective surface, said reflective means being adapted to reflect measurement optical beams incident upon said surface through said window and test material back through test material and said window.

5. The apparatus set forth in claim 4 wherein said mounting means comprises means which are relatively thin in a direction transverse to material flow as compared with the transverse dimension of said conduit.

6. The apparatus set forth in claim 4 wherein said mounting means comprises interlocking orthogonal plates having outer edges operatively engaging said conduit and means at said outer edges for engaging said tube and holding said tube adjacent said window.

7. The apparatus set forth in claim 6 wherein said means for adjusting the spacing between said reflective surface and said window comprises means for selectively disengaging said plates from said conduit, said plates being rotatable about said conduit axis when disengaged from said conduit to rotate said tube axis about said conduit axis and to thereby vary the spacing between said window and said reflective surface.

8. The apparatus set forth in claim 4 wherein said means for adjusting the spacing between said reflective surface and said window comprises means for rotating said tube axis about said conduit axis and to thereby vary the spacing between said reflective surface and said window.

9. The apparatus set forth in claim 8 wherein said mounting means is adapted to engage an opposing inner surface of said conduit, and wherein said means for adjusting the spacing between said reflective surface and said window comprises means for selectively disengaging said mounting means from said conduit surface, said mounting means being rotatable about the axis of said conduit when disengaged from said conduit to rotate said axis of said tube about said conduit axis.

10. The apparatus set forth in claim 8 wherein said window comprises an opening in said conduit wall, a translucent cylinder, and means mounting said translucent cylinder within said conduit in sealing engagement with said cylinder and conduit.

11. The apparatus set forth in claim 10 wherein said translucent cylinder is mounted coaxially with said conduit.

* * * * *